United States Patent [19]

Laas et al.

[11] Patent Number: 5,143,994
[45] Date of Patent: Sep. 1, 1992

[54] POLYISOCYANATE MIXTURE, A PROCESS FOR ITS PREPARATION AND ITS USE IN POLYURETHANE COATING COMPOSITIONS

[75] Inventors: Hans J. Laas, Cologne; Reinhard Halpaap, Odenthal-Gloebusch; Josef Pedain, Cologne; Jürgen Mosbach, Bergisch Gladbach, all of Fed. Rep. of Germany

[73] Assignee: Bayer Aktiengesellschaft, Leverkusen, Fed. Rep. of Germany

[21] Appl. No.: 759,315

[22] Filed: Sep. 13, 1991

[30] Foreign Application Priority Data

Sep. 20, 1990 [DE] Fed. Rep. of Germany ....... 4029809

[51] Int. Cl.$^5$ ............................................. C08G 18/74
[52] U.S. Cl. ..................... 528/45; 540/202; 252/182.2; 252/182.21; 528/67; 528/73
[58] Field of Search ............... 540/202; 252/182.2, 252/182.21; 528/45, 67, 73; 548/950

[56] References Cited

U.S. PATENT DOCUMENTS

| | | | |
|---|---|---|---|
| 4,419,513 | 12/1983 | Breidenbach et al. | 544/222 |
| 4,463,154 | 7/1984 | Disteldorf et al. | 528/45 |
| 4,476,054 | 10/1984 | Disteldorf et al. | 544/222 |
| 4,595,534 | 6/1986 | Scholl | 540/202 |
| 4,614,785 | 9/1986 | Richter et al. | 528/454 |
| 4,668,780 | 5/1987 | Disteldorf et al. | 540/202 |
| 4,912,210 | 3/1990 | Disteldorf et al. | 540/202 |
| 4,929,724 | 5/1990 | Engbert et al. | 540/202 |
| 4,994,541 | 2/1991 | Dell et al. | 528/51 |

FOREIGN PATENT DOCUMENTS 1934763 1/1971 Fed. Rep. of Germany .
1153815 5/1969 United Kingdom .

*Primary Examiner*—Maurice J. Welsh
*Assistant Examiner*—Rachel Johnson
*Attorney, Agent, or Firm*—Joseph C. Gil; Thomas W. Roy

[57] ABSTRACT

The present invention relates to polyisocyanate mixtures prepared from 1,6-diisocyanatohexane (HDI) and 1-isocyanato-3,3,5-trimethyl-5-isocyanatomethyl cyclohexane (IPDI), which have a uretdione content (calculated as $C_2N_2O_2$) of 8 to 25% by weight and an isocyanurate content (calculated as $C_3N_3O_3$) of not more than 24% by weight and contain a) 20 to 60% by weight of uretdione diisocyanates
b) 0 to 40% by weight of isocyanurate triisocyanates
c) 15 to 60% by weight of higher homologues of the polyisocyanates of components a) and b) containing more than one uretdione ring and/or isocyanurate ring and
d) a total of not more than 1% by weight of (HDI) and (IPDI).

The present invention also relates to a process for the preparation of these polyisocyanate mixtures and to their use, optionally blocked with blocking agents for isocyanate groups, as the isocyanate component in polyurethane coating compositions.

9 Claims, No Drawings

POLYISOCYANATE MIXTURE, A PROCESS FOR ITS PREPARATION AND ITS USE IN POLYURETHANE COATING COMPOSITIONS

BACKGROUND OF THE INVENTION

1. Field of the Invention

The invention relates to a new polyisocyanate mixture containing uretdione diisocyanates and prepared from mixtures of 1,6-diisocyanatohexane (HDI) and 1-isocyanato-3,3,5-trimethyl-5-isocyanatomethylcyclohexane (IPDI), a process for the preparation of this polyisocyanate mixture and its use for the production of polyurethane surface coatings.

2. Description of the Prior Art

The preparation of polyisocyanates containing uretdione groups by partially dimerizing aliphatic diisocyanates in the presence of suitable catalysts is known. DE-OS (German Published Specification) 3,030,513 describes the dimerization of IPDI using tris-(dialkylamino)-phosphines as the catalyst. According to DE-OS 3,227,779, the uretdiones of 2-methyl-1,5-diisocyanatopentane and 2-ethyl-1,4-diisocyanatobutane can be prepared in the same manner. The process of DE-OS 3,437,635 describes the use of H-active organic co-catalysts, such as alcohols or amines, for the dimerization of other aliphatic diisocyanates, such as HDI. However, tris-(dimethylamino)-phosphine is known to oxidize very rapidly in the presence of atmospheric oxygen to form the carcinogenic hexamethylphosphoric acid triamide which prohibits the commercial use of this catalyst.

Lewis acids, such as boron trifluoride or antimony pentafluoride, are proposed as dimerization catalysts for aliphatic diisocyanates in DE-OS 1,670,720 and 3,420,114. These processes have not become established, inter alia, because of the highly corrosive action of these catalysts.

According to DE-OS 3,739,549, dialkylamino-substituted pyridines, such as p-dimethylaminopyridine (DMAP), are suitable catalysts for the preparation of pure uretdiones from aliphatic diisocyanates. However, according to our own experiments, the products obtained from HDI and IPDI by this process display a marked intrinsic coloration, which renders them unsuitable for use as surface coating polyisocyanates.

The method known the longest for the dimerization of aliphatic diisocyanates comprises their modification with the aid of tertiary phosphines, preferably with trialkylphosphines. This is the subject matter of DE-OS 1,670,720 and 1,934,763, and of U.S. Pat. No. 4,614,785. The products obtained in this manner always contain, in addition to uretdione groups, a greater or lesser content of isocyanurate groups, and are relatively dark in color. However, further experiments have constantly been undertaken to improve the process.

Low-viscosity polyisocyanates which contain uretdione groups and have a low color number can be prepared from HDI by the urethanization of a portion of the isocyanate groups with suitable alcohols before or during the oligomerization reaction and treatment of the resin obtained after thin film distillation with organic peroxides, as described in DE-OS 3900053. These products are particularly suitable for use in light-fast one- or two-component polyurethane surface coatings, but cannot meet all the necessary requirements.

Surface coating polyisocyanates based on HDI, in particular diisocyanates also containing uretdione groups and based on HDI, are inferior to the corresponding polyisocyanates based on IPDI with regard to the resistance of the coatings obtained from the polyisocyanates to weathering. The diisocyanates which contain uretdione groups and are based on HDI are moreover unsuitable as the starting material for the preparation of powder coatings, for example, because of their low viscosity. However, diisocyanates which contain uretdione groups and are based on IPDI are suitable for this application as demonstrated in, for example, EPA 0,045,998. However, the disadvantage of these uretdione diisocyanates is their poor production rates. The dimerization of IPDI with the trialkylphosphine catalysts preferably employed for the dimerization of aliphatic diisocyanates requires relatively high catalyst concentrations (1 to 3%) and very long reaction times (8 days to 8 weeks) as disclosed in DE-OS 1,934,763.

An object of the present invention is to provide new polyisocyanates containing uretdione groups which are predominantly based on dimerized IPDI and combine the good surface coating properties known of surface coating polyisocyanates based on IPDI and at the same time can be prepared in high space-time yields.

This object may be achieved by the process according to the present invention, described below in more detail, for the preparation of the new polyisocyanate mixtures. This process is based on the surprising observation that polyisocyanates which contain uretdione groups and in which a very high proportion of the cycloaliphatic diisocyanate is incorporated can be prepared very easily from mixtures of HDI and IPDI having a comparatively low content of HDI by modification with trialkylphosphines.

Even the preparation of highly viscous to solid products under conditions which are appropriate in practice, i.e., low catalyst concentrations and relatively short reaction times, is made possible in this manner. Some of the above-mentioned publications, for example, U.S. Pat. No. 4,614,785 and DE-OS 3,420,114, 3,739,549 and 3,900,053, disclose long lists of suitable (cyclo)aliphatic diisocyanates and indicate that mixtures of these isocyanates can also be employed for the dimerization. However, it would not be possible for the skilled artisan to ascertain from these teachings that by admixing HDI to IPDI the reaction times for the preparation of uretdiones can be shortened drastically, even at a very high content of IPDI in the starting mixture, and that a large amount of IPDI can be incorporated into the polyisocyanate as demonstrated in the examples below. Based on the prior art these results are surprising since on the basis of the large difference in the reactivity of HDI and IPDI, it would be expected that the pure HDI uretdione and not an oligomer having a high IPDI content would preferentially be formed from mixtures of the two diisocyanates.

SUMMARY OF THE INVENTION

The present invention relates to polyisocyanate mixtures which have a uretdione content (calculated as $C_2N_2O_2$) of 8 to 25% by weight and an isocyanurate content (calculated as $C_3N_3O_3$) of not more than 24% by weight and contain a) 20 to 60% by weight of uretdione diisocyanates corresponding to formula I

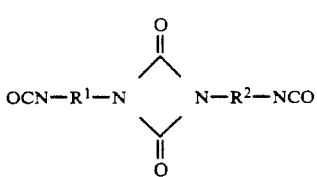

b) 0 to 40% by weight of isocyanurate triisocyanates corresponding to formula II

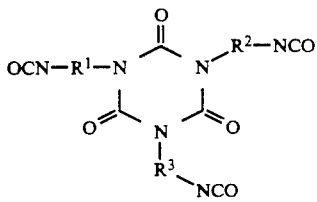

c) 15 to 60% by weight of higher homologues of polyisocyanates I and/or II containing more than one uretdione ring and/or isocyanurate ring and d) a total of not more than 1% by weight of 1,6-diisocyanatohexane (HDI) and 1-isocyanato-3,3,5-trimethyl-5-isocyanatomethyl cyclohexane (IPDI), wherein the percentages of a), b), c) and d) add up to 100, based on the total weight of a), b), c) and d) and wherein $R^1$, $R^2$ and $R^3$ may be identical or different and represent the hydrocarbon radicals linking the isocyanate groups of HDI or IPDI, in the latter case the isocyanate groups being linked to the cycloaliphatic ring, provided that at least 15 mole % and not more than 95 mole % of the radicals mentioned represent hexamethylene radicals.

The present invention also relates to a process for the preparation of these polyisocyanate mixtures by dimerizing a portion of the isocyanate groups of a mixture of IPDI and HDI in a molar ratio of 1:9 to 9:1 in the presence of a catalyst which accelerates the dimerization of isocyanate groups, terminating the dimerization reaction after 10 to 60% of the isocyanate groups present in the starting mixture have reacted and subsequently removing the unreacted diisocyanate excess by thin film distillation down to a residual content of not more than 1% by weight.

The invention finally also relates to the use of the new polyisocyanate mixtures, optionally blocked with blocking agents for isocyanate groups, as the isocyanate component in polyurethane coating compositions.

DETAILED DESCRIPTION OF THE INVENTION

Starting materials for the process according to the invention are HDI and IPDI, which are employed in the molar ratio of 1:9 to 9:1, preferably 1:7 to 7:1.

Particularly suitable dimerization catalysts for the process according to the invention are tertiary organic phosphines, such as those described in U.S. Pat. No. 4,614,785 (the disclosure of which is herein incorporated by reference) at column 4, lines 11 to 47. Preferred tertiary phosphines are tri-n-butylphosphine and tri-n-octylphosphine. All other known dimerization catalysts may also be used as catalysts for the process according to the invention.

Examples of such dimerization catalysts include the tris-(dialkylamino)-phosphines disclosed in DE-OS 3,030,513, 3,227,779 and 3,437,635; antimony pentafluoride according to DE-OS 3,420,114; boron trifluoride in accordance with DE-OS 1,670,720; and p-dimethylaminopyridine according to DE-OS 3,739,549.

The dimerization catalysts are employed in amounts of 0.01 to 5, preferably 0.1 to 3% by weight, based on the starting isocyanate mixture. If tertiary phosphines are employed as catalysts, these are employed in an amount of 0.1 to 5, preferably 0.2 to 2% by weight, based on the diisocyanate mixture employed.

In addition to these catalysts, co-catalysts can also be employed in the process according to the invention. Co-catalysts which are suitable are low molecular weight mono or polyhydric alcohols, in particular those having a molecular weight of 32 to 200, and mixtures of such alcohols. Examples of suitable alcohols include methanol, ethanol, n-propanol, isopropanol, n-butanol, n-hexanol, 2-ethyl-1-hexanol, ethylene glycol, propylene glycol, the isomeric butanediols, hexanediols and octanediols, diethylene glycol, dipropylene glycol, glycerol, trimethylolpropane and mixtures of these alcohols. The co-catalysts are employed, if at all, in amounts of 0.1 to 5, preferably 0.5 to 3% by weight, based on the weight of the starting isocyanate mixture.

Catalyst poisons which are suitable for terminating the reaction include alkylating agents such as dimethyl sulphate or methyl p-toluenesulphonate; acylating agents such as benzoyl chloride; acids such as perfluorobutanesulphonic acid; sulphur; and sulphonyl isocyanates, e.g., those mentioned in U.S. Pat. No. 4,614,785 (which is herein incorporated by reference) at column 5, line 27 to column 6, line 35. The amount of catalyst poison required for terminating the reaction depends upon the amount of catalyst used. An equimolar amount of the catalyst poison, based on the dimerization catalyst present at the start of the reaction, is generally employed. Nevertheless, if catalyst losses which occur during the reaction are taken into account, 20 to 80 equivalent percent of the catalyst poison, based on the equivalents of catalyst originally employed, should be sufficient to terminate the reaction.

The process according to the invention can be carried out in bulk or in the presence of solvents which are inert towards isocyanate groups. Examples of suitable solvents are hexane, toluene, xylene, chlorobenzene, ethyl acetate, butyl acetate, ethylglycol acetate, propylene glycol monomethyl ether acetate, acetone, methyl isobutyl ketone, methylene chloride, N-methylpyrrolidone or any desired mixtures of such solvents.

For carrying out the process according to the invention, a mixture of the starting diisocyanates is heated to a temperature of 20° to 100° C., preferably 40° to 70° C., optionally under an inert gas, such as nitrogen, and optionally in the presence of a suitable solvent. The optional alcoholic co-catalyst also can then be mixed in. During or after the urethanization reaction a dimerization catalyst of the type mentioned by way of example is added in the above-mentioned amount and the reaction temperature is maintained within a temperature range of 40° to 120° C., preferably 50° to 80° C., by a suitable measure (heating or cooling). The reaction has essentially ended when a degree of oligomerization of 10 to 60%, preferably 10 to 40%, has been reached. "Degree of oligomerization" is defined as the percentage of isocyanate groups present in the starting mixture which is consumed during the reaction according to the invention (in particular by dimerization and trimerization and, if alcoholic co-catalysts are also used, by urethanization). The degree of oligomerization is generally obtained after a reaction time of 1 to 48, preferably 2 to 24 hours. The reaction can be terminated by the addition of a catalyst poison and/or by brief heating of the reaction mixture to temperatures above 80° C., preferably above 120° C.

The reaction mixture is then freed from volatile constituents (excess monomers and any solvents) under a high vacuum, preferably in a thin film evaporator. The polyisocyanate mixtures according to the invention are obtained as the distillation residue. The polyisocyanate mixtures according to the invention thus obtained are virtually colorless polyisocyanates. Their consistency depends above all on the ratio of HDI to IPDI.

The ratio of HDI to IPDI radicals in the mixtures according to the invention can be determined from the molar composition of the diisocyanate mixture recovered. It is found that HDI is somewhat more reactive than IPDI under the conditions of the process according to the invention, which is why the ratio of HDI to IPDI radicals in the mixtures according to the invention shifts in favor of the hexamethylene radical when compared to the composition of the starting mixture. This happens as a function of the reaction conditions such as temperature, catalyst concentration and degree of oligomerization.

The consistency of the process products according to the invention predominantly depends upon the ratio of the diisocyanate radicals. Products having an HDI content of less than 40% by weight are in general highly viscous, while those having a higher HDI content are liquid at room temperature. The polyisocyanate mixtures according to the invention which have a high IPDI content and a viscosity of at least 50,000 mPa.s at 23° C. are often solid substances at room temperature when blocked with suitable blocking agents, in particular with ε-caprolactam, and as such are suitable as crosslinking agents for powder coatings compositions.

The NCO content of the products according to the invention depends upon their composition, but is generally 15 to 23% by weight, preferably 17 to 21% by weight.

Based on the composition of the products according to the invention and the fact that it is virtually impossible to dimerize IPDI under the conditions of the process according to the invention (comparison experiment), it can be concluded that the products according to the invention are predominantly true mixed dimers corresponding to the above-mentioned formula. However, this does not exclude the presence of "homooligomers" of the two diisocyanates.

These considerations and gel chromatography analyses demonstrate that the polyisocyanate mixtures according to the invention have the composition previously mentioned. The preferred polyisocyanate mixtures according to the invention have an NCO content of 17 to 21% by weight, a uretdione content ($C_2N_2O_2$) of 10 to 20% by weight and an isocyanurate content ($C_3N_3O_3$) of 0 to 20% by weight and contain a) 25 to 55% by weight of uretdione diisocyanates corresponding to formula I, b) to the extent of 0 to 30% by weight of isocyanurate triisocyanates corresponding to formula II, c) 20 to 55% by weight of higher homologues of the polyisocyanates mentioned under a) and b) containing more than one uretdione ring and/or more than one isocyanurate ring and d) a total of not more than 0.5% by weight of monomeric HDI and IPDI.

The mixtures according to the invention are useful starting materials in combination with a component containing at least two isocyanate-reactive groups for the preparation of polyurethane plastics by the polyaddition process, in particular for the preparation of one- or two-component polyurethane coatings. When blocked with known blocking agents the mixtures according to the invention are useful starting materials for two-component polyurethane stoving enamels.

Preferred reaction partners for the mixtures according to the invention for the preparation of polyurethane coatings are the polyhydroxy polyesters, polyhydroxy polyethers, polyhydroxypolyacrylates, polycarboxylic acids and optionally the known low molecular weight, polyhydric alcohols. Polyamines, in particular in blocked form as polyketimines, or oxazolidines are also reaction partners which can be used for the mixtures according to the invention.

The ratios of the amounts are in general chosen so that 0.8 to 3, preferably 0.9 to 1.1, hydroxyl, amino and/or carboxyl groups are present for each isocyanate group; the isocyanate groups may be blocked if desired.

Catalysts may be used to accelerate the curing. These catalysts are known and include tertiary amines such as triethylamine, pyridine, methylpyridine, benzyldimethylamine, N,N-endoethylenepiperazine, N-methylpiperidine, pentamethyldiethylenetriamine, N,N-dimethylaminocyclohexane and N,N'-dimethylpiperazine; and metal salts such as iron(III) chloride, zinc chloride, zinc 2-ethylcaproate, tin(II) ethylcaproate, dibutyltin-(IV) dilaurate and molybdenum glycolate.

When the mixtures according to the invention are used in stoving enamels, their NCO groups are completely or partly blocked in a known manner. The polyisocyanate mixture is reacted with a suitable blocking agent, preferably at elevated temperature, and optionally in the presence of a suitable catalyst.

Examples of suitable blocking agents include monophenols (phenol and cresols), tertiary alcohols (t.-butanol and dimethylphenylcarbinol), readily enolizable compounds (acetoacetates and malonic acid derivatives), secondary aromatic amines (N-methylaniline and N-phenylxylidine), imides (succinimide), lactams (ε-caprolactam and -valerolactam), oximes (butanone oxime and cyclohexanone oxime), mercaptans (methyl mercaptan and ethyl mercaptan) and triazoles (IH-1,2,4-triazole).

To prepare the surface coating binders the optionally blocked polyisocyanate, polyfunctional isocyanate-reactive component, catalyst and optionally known additives (such as pigments, fillers, dyestuffs and flow control agents) are mixed thoroughly with one another and homogenized on a customary mixing unit (for example, on a sand mill) either with or without solvents and diluents.

Suitable solvents include the known coating solvents such as ethyl acetate, butyl acetate, ethylene glycol monomethyl or -ethyl ether acetate, 1-methoxypropyl-2-acetate, 2-butanone, 4-methyl-2-pentanone, cyclohexanone, toluene, xylene, solvent naphtha and mixtures thereof. However, solvents (such as N-methylpyrrolidone or N-methylcaprolactam) and plasticizers (such as those based on phosphoric acid esters, sulphonic acid esters and phthalic acid esters) are also suitable.

The paints and coating agents can be applied to the object to be coated in solution or from the melt or in solid form by known methods such as brushing, rolling, pouring, spraying, the whirl sintering process or electrostatic powder spraying.

The essential advantage of the products according to the invention is that by a suitable choice of the molar ratio of the two diisocyanates in the starting mixture, the properties of the products can be optimized to suit the particular intended use. For example, HDI/IPDI mixed dimers having a high HDI content combine the advantage of the low viscosity of the pure HDI uretdiones with the good hardness of coatings produced from cycloaliphatic dimers. Alternatively, HDI/IPDI mixed dimers having a high IPDI content have the high viscosities of pure cycloaliphatic uretdiones, especially in blocked form, for use in powder coating compositions which are preferably applied by the electrostatic spraying process. At the same time, the coatings prepared from them exhibit a certain flexibility from the HDI content.

The following examples serve to further illustrate the invention. All parts and percentages are by weight, unless otherwise indicated.

The percentage of uretdione groups in the product was determined by hot titration of the NCO content (reflux for 3 hours in o-dichlorobenzene). The content of isocyanurate groups was calculated from the nature and amount of the starting materials and from the isocyanate and uretdione content of the product.

The IPDI content in the product was also calculated from the composition of the starting materials and from the excess diisocyanate distilled off. In some examples the content of uretdione diisocyanate and triisocyanato monoisocyanurate (mole %) was additionally determined by gel chromatography.

heated to 60° C. After a reaction time of 7 hours, the NCO content of the mixture had fallen to 38.5%. The reaction was terminated by the addition of 2.6 g of methyl p-toluenesulphonate (MTS) and heating at 80° C. for one hour. After the unreacted diisocyanate mixture had been distilled off in a thin film evaporator at 140° C. under a pressure of 0.05 mbar, a virtually colorless dimerization product having an NCO content of 20.7% and a viscosity of 270 mPa.s (23° C.) was obtained. The content of free HDI was 0.16% and the content of free IPDI was 0.17%. An IPDI content of 7 mole % can be determined for the reaction product from the composition of the diisocyanate mixture recovered. Hot titration of the NCO content found a content of uretdione groups of 12.4%. The IR spectrum of the product showed intensive bands for isocyanate and uretdione groups at 2272 and 1767 cm$^{-1}$, while the characteristic band of isocyanurates at 1690 cm$^{-1}$ was of only minor significance.

EXAMPLES 2 to 9

The reactions were carried out as described in Example 1. The composition of the starting mixtures, the reaction parameters and the characteristic data of the products are listed in Table 1.

TABLE 1

| Example | 2 | 3 | 4 | 5 | 6 | 7 | 8 | 9 |
|---|---|---|---|---|---|---|---|---|
| Starting mixture | | | | | | | | |
| HDI (g) | 1000 | 1000 | 800 | 454 | 267 | 267 | 202 | 67 |
| IPDI (g) | 440 | 440 | 1050 | 1400 | 1407 | 1407 | 1510 | 799 |
| HDI:IPDI (molar ratio) | 3:1 | 3:1 | 1:1 | 3:7 | 1:4 | 1:4 | 15:85 | 1:9 |
| Catalyst[a] | TBP | TOP | TBP | TOP | TBP | TOP | TOP | TBP |
| Reaction | | | | | | | | |
| Reaction time (hours) | 4.5 | 8 | 6 | 20 | 26 | 22 | 48 | 48 |
| % NCO of crude product | 39.3 | 35.7 | 37.3 | 35.4 | 32.9 | 32.3 | 32.4 | 32.7 |
| Distillation | | | | | | | | |
| Temperature (°C.) | 135 | 135 | 135 | 140 | 135 | 140 | 135 | 135 |
| Pressure (mbar) | 0.04 | 0.01 | 0.01 | 0.07 | 0.01 | 0.01 | 0.07 | 0.01 |
| Resin | | | | | | | | |
| % NCO | 20.7 | 20.5 | 19.3 | 17.8 | 18.1 | 17.7 | 17.6 | 17.4 |
| Viscosity (mPa·s/23° C.) | 375 | 500 | 1680 | 25400 | 120000 | >150000 | >200000 | >200000 |
| free HDI (%) | 0.17 | 0.10 | 0.09 | 0.11 | 0.04 | 0.07 | 0.09 | 0.03 |
| free IPDI (%) | 0.13 | 0.15 | 0.31 | 0.28 | 0.11 | 0.37 | 0.39 | 0.42 |
| Uretdione content (%) | 16.6 | 16.4 | 13.9 | 12.7 | 12.7 | 14.1 | 13.7 | 13.6 |
| Isocyanurate content (%) | 10.5 | 10.3 | 11.9 | 11.8 | 10.2 | 9.2 | 9.8 | 9.5 |
| IPDI content (mole %) | 18 | 23 | 40 | 63 | 74 | 74 | 73 | 78 |
| Uretdione diisocyanate (%) | 41.5 | — | — | 36.8 | — | 31.5 | 43.7 | — |
| Triisocyanatomono-isocyanurate (%) | 22.9 | — | — | 21.9 | — | 22.6 | 24.6 | — |
| Higher homologues (%) | 35.6 | — | — | 41.3 | — | 45.9 | 31.7 | — |
| IR (cm$^1$) | | | | | | | | |
| NCO | 2270 | 2271 | 2268 | 2261 | 2261 | 2261 | 2259 | 2257 |
| Uretdione | 1766 | 1767 | 1767 | 1767 | 1767 | 1767 | 1766 | 1766 |
| Isocyanurate | 1690 | 1690 | 1691 | 1692 | 1692 | 1692 | 1691 | 1693 |

EXAMPLES

Example 1

17.3 g of 2,2,4-trimethyl-1,3-pentanediol (TMPD) and 5.2 g of tri-n-octylphosphine were stirred in succession into a mixture of 1512 g (9 moles) of HDI and 222 g (1 mole) of IPDI at 50° C. and the mixture was then Explanation of the above table a) TBP = tri-n-butylphosphine;
TOP = tri-n-octylphosphine In each case the catalyst was used in an amount of 0.3% by weight, based on the total weight of diisocyanate starting material.

In each case TMPD was added as the cocatalyst in an amount of 1%, based on the total weight of diisocyanate starting material.

MTS was used as the catalyst poison in an equimolar amount, based on weight of the catalyst.

Comparison Example 10 g of TMPD and 3 g of TBP were added in succession to 1000 g (4.5 moles) of IPDI at 50° C., and the mixture was then heated to 60° C. and kept at this temperature. The NCO content of the reaction mixture dropped from an initial value of 37.8% to 36.5% in the course of 24 hours and remained constant for a further 48 hours. The degree of dimerization was 1.35%.

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A polyisocyanate mixture which has a uretdione content (calculated as $C_2N_2O_2$) of 8 to 25% by weight and an isocyanurate content (calculated as $C_3N_3O_3$) of not more than 24% by weight and comprises
   a) 20 to 60% by weight of a uretdione diisocyanate corresponding to formula I

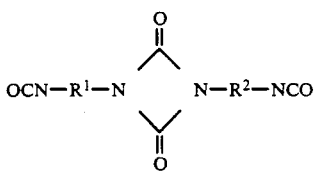

b) 0 to 40% by weight of an isocyanurate triisocyanate corresponding to the formula II

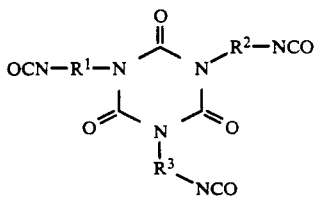

c) 15 to 60% by weight of higher homologues of the polyisocyanates corresponding to formulas I and II containing more than one uretdione ring and/or isocyanurate ring and
   d) a total of not more than 1% by weight of 1,6-diisocyanatohexane (HDI) and 1-isocyanato-3,3,5-trimethyl-5-isocyanatomethyl cyclohexane (IPDI), wherein the percentages of a), b), c) and d) add up to 100, based on the weight of a), b), c) and d), and wherein
      $R^1$, $R^2$ and $R^3$ are identical or different and represent the hydrocarbon radicals linking the isocyanate groups of HDI or IPDI, in the latter case the isocyanate groups being linked to the cycloaliphatic ring, provided that at least 15 mole % and not more than 95 mole % of the radicals mentioned represent hexamethylene radicals.

2. A process for the preparation of a polyisocyanate mixture which has a uretdione content (calculated as $C_2N_2O_2$) of 8 to 25% by weight and an isocyanurate content (calculated as $C_3N_3O_3$) of not more than 24% by weight and comprises
   a) 20 to 60% by weight of a uretdione diisocyanate corresponding to formula I

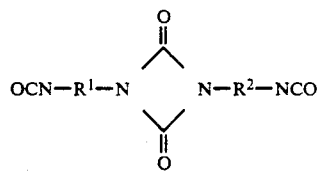

b) 0 to 40% by weight of an isocyanurate triisocyanate corresponding to the formula II

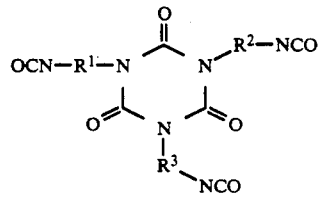

c) 15 to 60% by weight of higher homologues of the polyisocyanates corresponding to formulas I and II containing more than one uretdione ring and/or isocyanurate ring and
   d) a total of not more than 1% by weight of 1,6-diisocyanatohexane (HDI) and 1-isocyanato-3,3,5-trimethyl-5-isocyanatomethyl cyclohexane (IPDI), wherein the percentages of a), b), c) and d) add up to 100, based on the weight of a), b), c) and d), and wherein
      $R^1$, $R^2$ and $R^3$ are identical or different and represent the hydrocarbon radicals linking the isocyanate groups of HDI or IPDI, in the latter case the isocyanate groups being linked to the cycloaliphatic ring, provided that at least 15 mole % and not more than 95 mole % of the radicals mentioned represent hexamethylene radicals, which comprises dimerizing a portion of the isocyanate groups of a mixture of HDI and IPDI in the molar ratio of 1:9 to 9:1 in the presence of a catalyst which accelerates the dimerization of isocyanate groups, terminating the dimerization reaction after 10 to 60% of the isocyanate groups present in the starting mixture have reacted, and subsequently removing the unreacted diisocyanate excess by thin film distillation down to a residual content of not more than 1% by weight.

3. The process of claim 2 wherein said catalyst comprises an organic phosphine.

4. The process of claim 2 wherein the dimerization is carried out in the presence of co-catalyst comprising a mono- or polyhydric alcohol.

5. The process of claim 3 wherein the dimerization is carried out in the presence of co-catalyst comprising a mono- or polyhydric alcohol.

6. The process of claim 2 wherein said catalyst comprises tri-n-butylphosphine or tri-n-octylphosphine.

7. The process of claim 4 wherein said catalyst comprises tri-n-butylphosphine or tri-n-octylphosphine.

8. The process of claim 5 wherein said catalyst comprises tri-n-butylphosphine or tri-n-octylphosphine.

9. A polyurethane coating composition which comprises the polyisocyanate mixture of claim 1, optionally blocked with blocking agents for isocyanate groups, and a component containing at least two isocyanate-reactive groups.

* * * * *